United States Patent
Heibel et al.

(12)

(10) Patent No.: US 6,274,170 B1
(45) Date of Patent: Aug. 14, 2001

(54) COMPOUNDS FOR CARDIOVASCULAR TREATMENT COMPRISING MULTI-VITAMIN AND ANTI-PLATELET AGGREGATING AGENTS AND METHODS FOR MAKING AND USING THE SAME

(76) Inventors: Richard Heibel, 20 N. Port Royal Dr., Hilton Head Island, SC (US) 29928; John J. Abbott, 1500 Redfern Dr., Pittsburgh, PA (US) 15241

( * ) Notice: Subject to any disclaimer, the term of this patent is extended or adjusted under 35 U.S.C. 154(b) by 0 days.

(21) Appl. No.: 09/250,941

(22) Filed: Feb. 18, 1999

(51) Int. Cl.[7] .............................. A61K 9/58; A61K 9/60; A61K 9/62
(52) U.S. Cl. .................... 424/458; 424/461; 424/462; 514/772.3; 514/781; 514/782
(58) Field of Search .................... 424/464, 489, 424/474, 476, 480, 458, 482, 461, 462, 497, 494, 498, 481

(56) References Cited

U.S. PATENT DOCUMENTS

| 1,969,998 | 8/1934 | Wodlinger . |
|---|---|---|
| 3,914,419 | 10/1975 | Haeger et al. . |
| 4,753,926 | 6/1988 | Lucas et al. . |
| 4,760,080 | 7/1988 | Barron et al. . |
| 4,806,354 | 2/1989 | Green . |
| 4,937,234 | 6/1990 | Fahim . |
| 4,945,083 | 7/1990 | Jansen, Jr. . |
| 5,084,482 | 1/1992 | Hirsch et al. . |
| 5,118,505 | 6/1992 | Költringer . |
| 5,300,298 | 4/1994 | LaNoue . |
| 5,322,689 | 6/1994 | Hughes et al. . |
| 5,401,730 | 3/1995 | Sauvage et al. . |
| 5,541,220 | 7/1996 | Ismail . |
| 5,545,670 | 8/1996 | Bissbort et al. . |
| 5,563,126 | 10/1996 | Allen et al. . |
| 5,597,585 | 1/1997 | Williams et al. . |
| 5,626,883 | 5/1997 | Paul . |
| 5,626,884 | 5/1997 | Lockett . |
| 5,652,261 | 7/1997 | Ismail . |
| 5,656,620 | 8/1997 | Ismail . |
| 5,733,572 | 3/1998 | Unger et al. . |
| 5,770,215 | 6/1998 | Moshyedi . |
| 5,786,384 | 7/1998 | Ismail . |
| 5,795,873 | 8/1998 | Allen . |

OTHER PUBLICATIONS

Nelson and Forfar, Associations Between Drugs Administered During Pregnancy And Congenital Abnormalities of the Fetus, British Medical Journal, Mar. 6, 1971, pp. 523–527.

*Primary Examiner*—James M. Spear
(74) *Attorney, Agent, or Firm*—Alan G. Towner; Eckert Seamans Cherin & Mellott, LLC

(57) ABSTRACT

Compounds comprising multi-vitamins, zinc and an anti-platelet aggregating agent for the treatment of atherosclerotic cardiovascular disease (ASCVD) are disclosed. The compounds are provided in dosage form, and preferably include selected amounts of ascorbic acid, folic acid, vitamin E, vitamin B6 and vitamin B12. The anti-platelet aggregating agent preferably comprises aspirin. A protective coating is preferably provided between the aspirin and the other vitamin and mineral constituents. The dosages are effective in the treatment of ASCVD, and possess extended shelf lives.

64 Claims, 2 Drawing Sheets

COMPOUNDS FOR CARDIOVASCULAR TREATMENT COMPRISING MULTI-VITAMIN AND ANTI-PLATELET AGGREGATING AGENTS AND METHODS FOR MAKING AND USING THE SAME

FIELD OF THE INVENTION

The present invention relates to compounds for the prevention and treatment of diseases such as atherosclerotic cardiovascular disease (ASCVD). More particularly, the present invention encompasses a comprehensive approach including the use of anti-platelet aggregating agents in conjunction with certain vitamins and minerals which, in combination, have a positive effect on normalizing elevated homocysteine levels in vivo, and which impact free radicals with the use of anti-oxidants implicated in the initiation of atherosclerotic cardiovascular disease.

BACKGROUND INFORMATION

Atherosclerotic cardiovascular disease (ASCVD) is the leading cause of death in most industrial countries. This disease involves large, medium and small arteries throughout the body. In addition to family history, the atherogenic risk factors are known to include smoking, hypertension, diabetes mellitus, cholesterol abnormalities and homocysteinuria. The presence of each additional risk factor markedly aggravates the potential for development of the disease. Although seemingly diverse, the risk factors all damage the artery wall and effect formation of thrombosis.

In the aorta, the largest artery, the artery wall damage may lead to aortic aneurysm or embolism. ASCVD in medium and small arteries can result in sudden occlusion of the vessel or progressive narrowing of the arterial lumen. The symptoms of persons with this disease are dictated by the organs supplied by the effected arteries. Lumenal narrowing of the arteries supplying the heart with blood is called coronary artery disease (CAD). The symptoms include angina, unstable angina, myocardial infarction (MI) and sudden death. Cerebral vascular disease (CVD) symptoms include progressive neural deterioration, transient ischemic attack (TIA), seizures, and cerebral vascular accident (CVA), i.e., stroke. Kidney effects include hypertension, renal infarction and renal failure. Abdominal vascular insufficiency results in abdominal angina and bowel infarction. Peripheral vascular disease (PVD) symptoms include intermittent claudication, gangrene and amputation.

Because atherosclerosis greatly increases the risk of peripheral vascular disease, angina, stroke, some causes of neural degeneration, and heart attacks—the number one cause of death in the USA, a comprehensive approach is needed to address this problem. Despite the broad use of lipid lowering agents, individuals with elevated homocysteine levels are about four times more likely to die of cardiovascular disease than those with normal levels.

Currently accepted clinical treatment of ASCVD includes prescription medications such as beta blockers, angiotensin converting enzyme (ACE) inhibitors, calcium channel blockers, and cholesterol lowering medication. In addition, aspirin is prescribed by cardiologists in many ASCVD conditions. For example, in atherosclerotic heart disease (ASHD), there is evidence of protection from a second MI, if aspirin is used after the sentinel event. Risk of MI is decreased by approximately 50 percent. Vitamins are also currently prescribed by many cardiologists and endocrinologists with intent of preventing both primary (first event), and secondary events.

The affect of arterial thrombus formation contributes to vascular wall damage and acts as the terminal event in a condition like MI. Thrombus formation is a complex interaction of platelets, coagulation factors, and damage to the intima and endothelial layer of the artery wall. Certain risk factors and thrombosis on the vascular wall contribute to damage the inner vascular wall and expose vascular endothelium. Circulating platelets adhere to the exposed subendothelium collagen. The Von Willebrand factor binds platelets causing adhesion. This initiates a series of progressive events stimulating platelet aggregation, and includes prostaglandin H2 and thromboxane A2. Circulating fibrinogen converts to fibrin with the formation of fibrin strands which secure the platelet mass to the arterial wall. If the reaction ceases at this juncture, the artery wall has been weakened and can deteriorate again at any time, and the lumen of the vessel has been diminished to some degree. If the event is self propagating the vessel can occlude and result in infarction of the affected organ. In this overview of the intravascular process of clotting, it must be remembered that this is a delicate balance of the tendency of blood to lyse or clot based on relative amounts of chemicals and enzymes present in the artery wall and platelets. For example, platelet aggregation is mediated by prostacyclin. Prostacyclin is also a vasodilator and is thought to render the vessel lining inert to platelets. Thromboxane causes platelet aggregation and smooth muscle spasm in the arterial wall. Thus, TxA2 and prostacyclin have opposing effects on platelet aggregation and the regulation of thrombus formation is determined by their quantitative balance.

The compounds of the present invention contain a combination of vitamins to help decrease homocysteine levels and modify the oxidation of LDL cholesterol in the initiation of ASCVD. Even mild and moderate elevation of homocysteine levels have been demonstrated to induce cerebrovascular and CAD. Several mechanisms have been proposed including direct toxic effects of homocysteine levels on the vascular endothelium and in proliferation of arterial wall smooth muscle cells. Folate and B6 are required for the degradation of homocysteine to methionine. There is an inverse relation between serum folate and homocysteine levels. It has also been demonstrated that administering folate and B6 will lower homocysteine levels. Fatal CAD incidence is increased as folate level decreases. In one study approximately 28 percent of people had depressed serum folate levels.

Lipid peroxidation, oxidative modification of LDL cholesterol and free radicals are implicated in the initiation of atherosclerosis. LDL undergoes oxidative modification, giving origin to foam cells, a very early sate of atherosclerosis. Macrophages, the precursors of foam cells, can only take up the LDL if it has been oxidized. Oxidized LDL is highly toxic to cells and may be responsible for endothelial damage and destruction of smooth muscle cells. Fatty streaks, an accumulation of foam cells just beneath the arterial endothelium, are precursors of more significant lesions or blockage. The atherosclerotic process also shows an accumulation of lipid peroxidation in the blood and the arterial wall. Interventions that block oxidative modifications of LDL are the subject of multiple studies. If oxidative modification of LDL results in enhanced macrophage uptake, use of an appropriate antioxidant should protect LDL from oxidation, thereby decreasing fatty streaks in the artery wall.

U.S. Pat. No. 5,770,215 to Moshyedi discloses compositions consisting of aspirin and many different types of vitamins and minerals for use in inhibiting vascular occlusion.

Despite the above-noted approaches, a need still exists for an effective compound for treating ASCVD. This invention addresses such problems by lowering artery damaging amino acids while at the same time inhibiting cyclo-oxygenase to block platelet aggregation associated with thrombus formation. Furthermore, a need exists for such a compound which is stable and possesses long shelf life. The present invention has been developed in view of the foregoing, and to address other deficiencies of the prior art.

SUMMARY OF THE INVENTION

An aspect of the present invention is to provide a compound in dosage form which is effective in the treatment of ASCVD. The compound comprises an anti-platelet aggregating agent such as aspirin in combination with multiple vitamins including ascorbic acid, folic acid, vitamin E, vitamin B6 and vitamin B12. The compound further comprises zinc.

Another aspect of the present invention is to provide a compound for the treatment of ASCVD comprising an anti-platelet aggregating agent, zinc, and at least two vitamins selected from the group comprising ascorbic acid, folic acid, vitamin E, vitamin B6 and vitamin B12. The anti-platelet aggregating agent is preferably aspirin, and a protective coating is provided between the aspirin and the vitamins.

A further aspect of the present invention is to provide a method of making a compound for the treatment of ASCVD. The method includes the steps of providing zinc and selected vitamins such as ascorbic acid, folic acid, vitamin E, vitamin B6 and vitamin B12, and combining the zinc and multiple vitamins with an anti-platelet aggregating agent such as aspirin in dosage form. The method preferably includes the application of a protective coating between the aspirin and the remaining constituents of the dosage.

Another aspect of the present invention is to provide a method of treating an ASCVD patient by administering an effective amount of a compound dosage to the patient. The compound dosage comprises an anti-platelet aggregating agent such as aspirin in combination with zinc and multiple vitamins including ascorbic acid, folic acid, vitamin E, vitamin B6 and vitamin B12. A protective coating is preferably provided between the aspirin and the remaining constituents of the dosage.

These and other aspects of the present invention will be more apparent from the following description.

DETAILED DESCRIPTION

Figure 1:
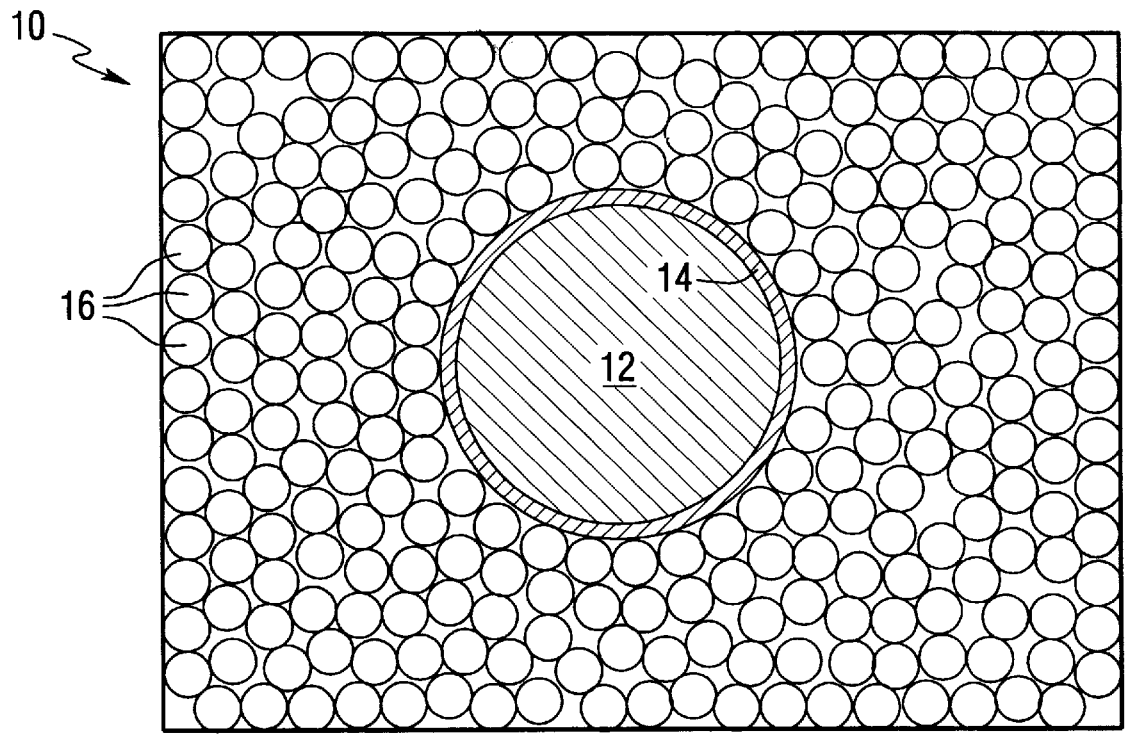
FIG. 1 is a partially schematic illustration of a multi-vitamin and aspirin compound dosage in accordance with an embodiment of the present invention.

The compounds of the present invention comprise a combination of vitamins and an anti-platelet aggregating agent such as aspirin in effective amounts for the treatment of coronary care patients. The multi-vitamin component of the compound preferably includes ascorbic acid, folic acid, vitamin E, vitamin B6 and vitamin B12. In addition, the compound preferably includes zinc, for example, in the form of zinc gluconate. These ingredients are combined with aspirin and/or other types of anti-platelet aggregating agents in a dosage form which is effective for the treatment of atherosclerotic cardiovascular diseases.

The dosage preferably comprises from about 90 to about 1,000 milligrams of vitamin C (ascorbic acid), more preferably from about 100 to about 150 milligrams. A particularly preferred amount of ascorbic acid is about 100 milligrams. Vitamin C is a powerful anti-oxidant that acts as a free radical scavenger. It increases the synthesis of interferon and stimulates key immune cells.

Folic acid preferably comprises from about 400 to about 1,000 micrograms of the dosage, more preferably from about 400 to about 800 micrograms. Folic acid acts as a coenzyme in DNA and RNA synthesis and is vital for protein metabolism. It is an essential component in the present formulation to reduce homocysteine levels. The action of folic acid is enhanced when vitamins B12 and C and zinc are present in adequate levels.

The dosage preferably comprises from about 200 to about 1,200 International Units of vitamin E (alpha tocopherol), more preferably from about 300 to about 800 International Units. A particularly preferred amount of vitamin E is 400 International Units. Vitamin E is a powerful anti-oxidant that prevents the oxidation of lipids. It helps prevent free radical damage, and reduces the risk of coronary artery disease. The presence of zinc in adequate concentration is necessary to maintain proper levels of vitamin E.

Vitamin B6 (pyridoxine) preferably comprises from about 3 to about 25 milligrams of the dosage, more preferably from about 10 to about 20 milligrams. A particularly preferred amount of vitamin B6 is about 15 milligrams. Vitamin B6 is an essential vitamin in the in vivo conversion of homocysteine, an atherogenic amino acid, to cysteine, a normal body component. Deficiencies of this vitamin contribute to an impaired reduction pathway via a redox couple, necessary for this biologic conversion.

The dosage preferably comprises from about 5 to about 500 micrograms of vitamin B12 (cyanocobalamin), more preferably from about 8 to about 100 micrograms. Vitamin B12 is essential in regulating the formation of red blood cells and enhances the utilization of iron. This vitamin works best in conjunction with adequate levels of folic acid and vitamin B6. The vitamin is linked to the production of acetylcholine.

The preferred compounds of the present invention combine the above-noted vitamins in a dosage form for the effective treatment of coronary diseases. Other supplements may optionally be included in the present compounds, such as choline, biotin, inositol, riboflavin, niacin, panothenic acid, vitamin K, rutin and/or coenzyme Q-10.

In accordance with the present invention, the compounds preferably include zinc. Zinc is a component of more than 100 enzymes and is vital for RNA and DNA synthesis. The body of an average person contains about 2.2 gm of zinc. It is a necessary component of the anti-oxidant enzyme superoxide dismutase which reduces the rate of cell destruction. Adequate levels of zinc are needed for the absorption of vitamin A and to maintain proper levels of vitamin E. Zinc gluconate is a particularly preferred form of zinc because of its improved absorption characteristics. The dosage preferably comprises from about 15 to about 100 milligrams of zinc gluconate, more preferably from about 30 to about 50 milligrams.

In addition to zinc, other minerals may optionally be added to the present compounds. For example, minerals such as magnesium, manganese, molybdenum, chromium, selenium, copper, iodine, calcium and/or potassium may be added.

In accordance with the present invention, suitable anti-platelet aggregating agents include aspirin, ibuprofen, flubiprofen, ketoprofen, naproxen, tolmetin, fenoprofen, piroxicam, sulindac and mefenamic acid. Typical dosages of such agents include 400 mg ibuprofen, 100 mg flubiprofen, 50 mg ketoprofen, 250 mg naproxen, 200 mg tolmetin, 300 mg fenoprofen, 10 mg piroxicam, 150 mg sulindac, or 250 mg mefenamic acid.

In accordance with the currently preferred embodiment of the present invention, the compounds include an effective amount of aspirin (acetylsalicylic acid) as the anti-platelet aggregating agent. Since therapeutic treatment of altering thrombus formation focuses on inhibition of platelet aggregation, aspirin is used in controlled amounts in accordance with the preferred embodiment of the present invention. Because aspirin effects both TxA2 and prostacyclin, the does of aspirin for arterial thrombosis prevention is optimized in accordance with the present invention. The dosage preferably comprises from about 25 to about 325 milligrams of aspirin, more preferably from about 50 to about 300 milligrams. In a particularly preferred embodiment, the aspirin comprises about 81 milligrams of the dosage. In another particularly preferred embodiment, the aspirin comprises about 162 milligrams of the dosage. Aspirin in controlled amounts blocks platelet aggregation by irreversibly inhibiting the platelet enzyme cyclo-oxygenase to prevent the formation of thromboxane A2. Because aspirin effects both TxA2 and prostacycline, the dose of aspirin for arterial thrombosis prevention is controlled in accordance with the present invention.

The preferred and more preferred ranges of the above-noted ingredients are listed in Table 1.

TABLE 1

| Ingredient | Preferred Amount | More Preferred Amount |
| --- | --- | --- |
| ascorbic acid | 90 to 1,000 milligrams | 100 to 150 milligrams |
| folic acid | 400 to 1,000 micrograms | 400 to 800 micrograms |
| vitamin E | 200 to 1,200 International Units | 300 to 800 International Units |
| vitamin B6 | 3 to 25 milligrams | 10 to 20 milligrams |
| vitamin B12 | 5 to 500 micrograms | 8 to 100 micrograms |
| zinc gluconate | 15 to 100 milligrams | 30 to 50 milligrams |
| aspirin | 25 to 325 milligrams | 50 to 300 milligrams |

In accordance with an embodiment of the present invention, the compound is provided in a stable dosage form in which unwanted interaction between the aspirin and the other ingredients is substantially prevented. This is achieved by providing a protective coating between the aspirin and the multiple vitamins. For example, a protective coating may be provided around the aspirin which minimizes or prevents deleterious reactions with the other vitamin and mineral ingredients. The protective coating preferably comprises at least one layer of wax, shellac, hydroxypropyl, methylcellulose phthalate, polyvinyl acetate phthalate and/or cellulose acetate phthalate. In a preferred embodiment, the protective coating comprises an enteric coating which may be applied to tablet formulations or to drug particles or granules used in the subsequent fabrication of capsules. The coatings are applied in single or multiple stages depending upon the desired effect. The coating systems can be either aqueous based or organic solvent based to resist breakdown in the low pH environment of the stomach.

FIG. 1 schematically illustrates a multi-vitamin and aspirin compound dosage 10 in accordance with an embodiment of the present invention. The dosage 10 may be provided in capsule form, or in any other suitable form. The dosage 10 includes a single aspirin unit 12 having a protective coating 14. The aspirin unit 12 is preferably provided in tablet form with an enteric protective coating 14. However, the aspirin unit 12 may be provided in other forms such as a capsule, caplet or microencapsulated pellets.

The dosage 10 includes vitamin and mineral constituents 16 in the preferred amounts listed previously. In the embodiment shown in FIG. 1, the vitamin and mineral constituents 16 are provided in loose powder form. However, the vitamin and mineral constituents 16 may be provided in other forms such as bilayer form, colloidal form or the like.

Figure 2:
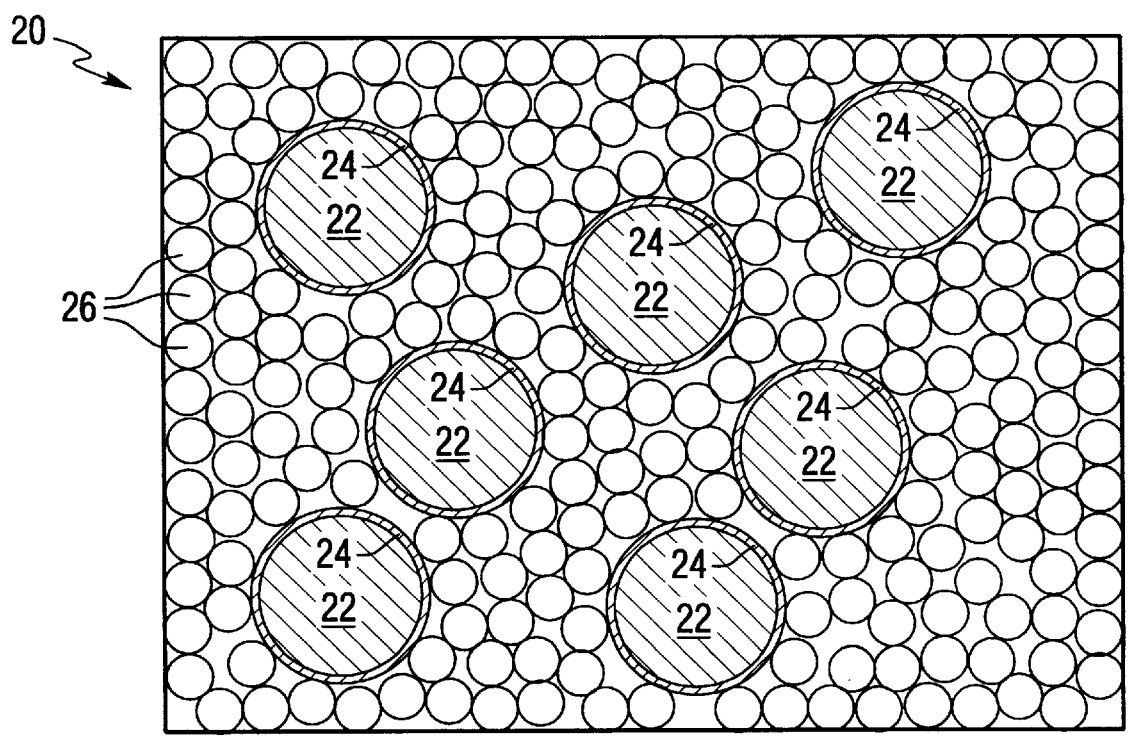
FIG. 2 is a partially schematic illustration of a multi-vitamin and aspirin compound dosage in accordance with another embodiment of the present invention.

FIG. 2 schematically illustrates a multi-vitamin and aspirin compound dosage 20 in accordance with another embodiment of the present invention. In this embodiment, the aspirin is provided as several individual units 22, each of which includes a protective coating 24. The dosage 20 also includes vitamin and mineral constituents 26. In this embodiment, the number and weight of the aspirin units 22 are controlled in order to provide the desired amount of aspirin in the dosage. Although the dosage 20 shown in FIG. 2 comprises a loose powder mixture of the vitamin and mineral constituents 26, other forms may be used as noted previously.

Figure 3:
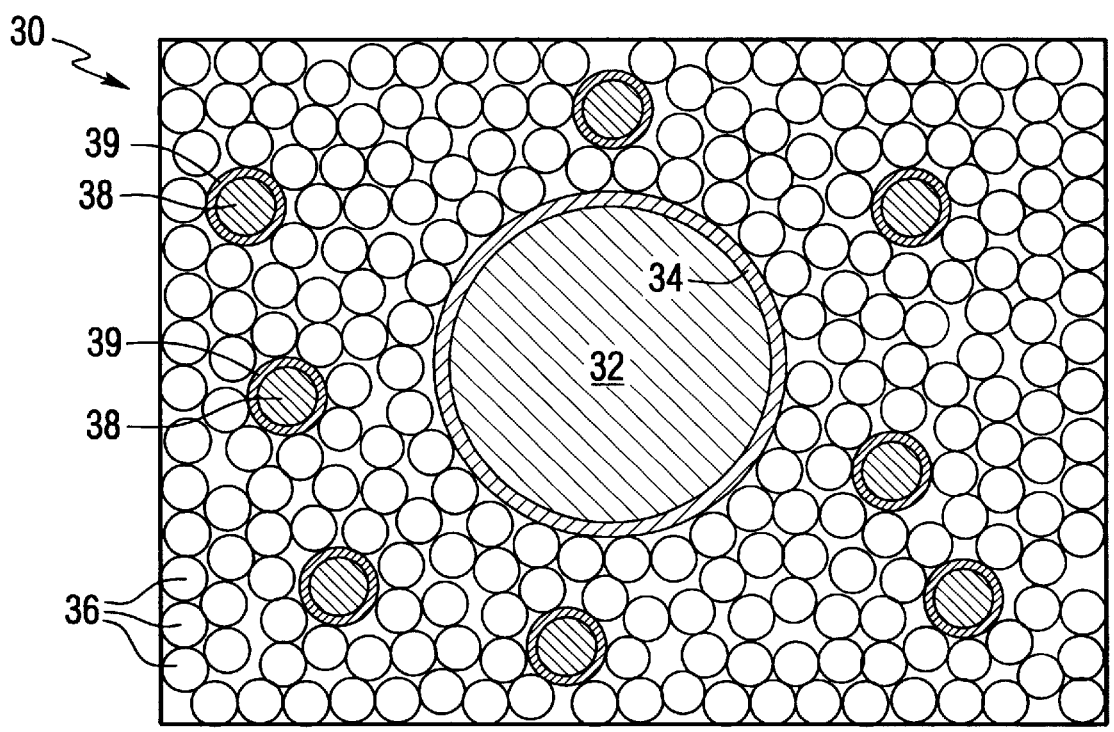
FIG. 3 is a partially schematic illustration of a multi-vitamin and aspirin dosage in accordance with a further embodiment of the present invention.

FIG. 3 schematically illustrates a multi-vitamin and aspirin compound dosage 30 in accordance with a further embodiment of the present invention. In this embodiment, the dosage 30 includes a single aspirin unit 32 having a protective coating 34. The dosage 30 also includes vitamin and mineral constituents 36 in the preferred amounts listed previously. However, at least one of the vitamin and/or mineral constituents 38 comprises a protective coating 39 which forms a barrier against unwanted reactions with the other vitamin and mineral constituents 36. The protective coating 39 may be the same as, or different from, the protective coating 34. As a particular example, the B vitamins, such as B12, may be provided with a protective coating in order to reduce or eliminate unwanted reactions with low pH ingredients such as ascorbic acid and aspirin. While both the aspirin 32 and vitamin/mineral constituent 38 are both provided with protective coatings in the embodiment shown in FIG. 3, the aspirin 32 may optionally be uncoated.

In accordance with a preferred embodiment of the present invention, the compound dosage is stable and possesses extended shelf life. By providing a protective coating between the aspirin and the vitamin and mineral constituents, unwanted reactions which reduce shelf life are prevented or minimized. For example, without the protective coating, the aspirin may react with vitamin B12 and folate, thereby lowering the effective amounts of aspirin and these B vitamins contained in the dosage.

In addition to maintaining the effective amount of aspirin and vitamin and mineral constituents in the dosage, the use of a protective coating in accordance with the present invention may reduce or eliminate the formation of deleterious reaction products resulting from the unwanted interaction between the aspirin and the vitamin and mineral constituents.

The protective coating preferably extends the shelf life of the dosage to at least 365 days, more preferably to about 720 days. As used herein, the term "shelf life" means the maintenance of at least 90 percent of label potency for a specified time.

The following examples are intended to illustrate various aspects of the present invention, and are not intended to limit the scope of the invention.

EXAMPLE 1

Multi-vitamin and aspirin compound dosages of the present invention were made as follows. Ascorbic acid powder was mixed with vitamin E succinate and zinc gluconate powders followed by the addition of folic acid, vitamin B6 and vitamin B12. In Formula No. 1, an unprotected aspirin tablet was then added to the mixture and enclosed in a gelatin capsule. In Formula No. 2, an enteric coated aspirin tablet was added to the mixture and enclosed in a gelatin capsule. The vitamin/mineral ingredients of the dosages are listed in Table 2. Formula No. 1 included 162 miligrams of aspirin, while Formula No. 2 included 81 milligrams of aspirin.

TABLE 2

| Aspirin (acetylsalicylic acid) | Vitamin/Mineral |
| --- | --- |
| 162 milligrams (Formula No. 1)<br>81 milligrams (Formula No. 2) | Ascorbic Acid - 100 milligrams<br>Folic Acid - 800 micrograms<br>Vitamin E - 400 International Units<br>Vitamin B6 - 15 milligrams<br>Vitamin B12 - 8 micrograms<br>Zinc Gluconate - 50 milligrams |

EXAMPLE 2

Heat testing and assay testing were performed as follows. Formula No. 1 was packaged in bottles of 30 and 120 in HDPE white bottles with a standard P/P cap with 75 m liner. Formula No. 2 was packaged in bottles of 30 in HDPE white bottles with a standard P/P cap with 75 m liner. Once packaged, the capsules were stored in approved stability chambers at accelerated conditions at 40 degrees centigrade/ 75 percent relative humidity for three months to determine stability. Standard assay methods were used to determine the contents of the formulations after the three month accelerated testing period ended. These included the use of HPLC and spectrophotometric measurements in an accredited laboratory using accepted methods of assay. The results of the accelerated aging tests and assay procedures revealed that the shelf life of Formula No. 2 with the coated aspirin was substantially longer than Formula No. 1, demonstrating a need for using protected aspirin to produce a formulation with a acceptable self life having improved commercial application.

The multi-vitamin and aspirin compounds of the present invention are preferably used to treat ASCVD patients by the administration of one or more oral dosages as described above. The dosages are preferably administered once or twice per day, but may be administered less or more often as appropriate.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound dosage for the treatment of atherosclerotic cardiovascular disease comprising:

ascorbic acid, folic acid, a minimum of about 200 International Units of vitamin E, vitamin B6 and vitamin B12 in therapeutic amounts effective for the treatment of atherosclerotic cardiovascular disease;

zinc; and an anti-platelet aggregating agent.

2. The compound dosage of claim 1, wherein the anti-platelet aggregating agent comprises at least one compound selected from the group consisting of aspirin, ibuprofen, flubiprofen, ketoprofen, naproxen, tolmetin, fenoprofen, piroxicam, sulindac and mefenamic acid.

3. The compound dosage of claim 1, wherein the anti-platelet aggregating agent comprises aspirin.

4. The compound dosage of claim 3, wherein the aspirin comprises from about 25 to about 325 milligrams.

5. The compound dosage of claim 1, wherein the zinc is provided in the form of zinc gluconate.

6. The compound dosage of claim 5, wherein the zinc gluconate comprises from about 15 to about 100 milligrams.

7. The compound dosage of claim 1, wherein the ascorbic acid comprises from about 90 to about 1,000 milligrams.

8. The compound dosage of claim 1, wherein the folic acid comprises from about 400 to about 1,000 micrograms.

9. The compound dosage of claim 1, wherein the vitamin E comprises from about 200 to about 1,200 International Units.

10. The compound dosage of claim 1, wherein the vitamin E comprises from about 300 to about 800 International Units.

11. The compound dosage of claim 1, wherein the vitamin B6 comprises from about 3 to about 25 milligrams.

12. The compound dosage of claim 1, wherein the vitamin B12 comprises from about 5 to about 500 micrograms.

13. The compound dosage of claim 1, wherein the dosage comprises from about 90 to about 1,000 milligrams of ascorbic acid, from about 400 to about 1,000 micrograms of folic acid, from about 200 to about 1,200 International Units of vitamin E, from about 3 to about 25 milligrams of vitamin B6, from about 5 to about 500 micrograms of vitamin B12, from about 15 to about 100 milligrams of zinc gluconate, and from about 25 to about 325 milligrams of aspirin.

14. The compound dosage of claim 1, wherein the dosage comprises from about 100 to about 150 milligrams of ascorbic acid, from about 400 to about 800 micrograms of folic acid, from about 300 to about 800 International Units of vitamin E, from about 10 to about 20 milligrams of vitamin B6, from about 8 to about 100 micrograms of vitamin B12, from about 30 to about 50 milligrams of zinc gluconate, and from about 50 to about 300 milligrams of aspirin.

15. The compound dosage of claim 1, wherein the dosage comprises about 100 milligrams of ascorbic acid, about 800 micrograms of folic acid, about 400 International Units of vitamin E, about 15 milligrams of vitamin B6, about 50 micrograms of vitamin B12, about 50 milligrams of zinc gluconate, and about 81 milligrams of aspirin.

16. The compound dosage of claim 1, wherein the dosage comprises about 100 milligrams of ascorbic acid, about 800 micrograms of folic acid, about 400 International Units of vitamin E, about 15 milligrams of vitamin B6, about 50 micrograms of vitamin B12, about 50 milligrams of zinc gluconate, and about 162 milligrams of aspirin.

17. The compound dosage of claim 3, further comprising a protective coating between the aspirin and the multiple vitamins.

18. The compound dosage of claim 17, wherein the protective coating substantially surrounds the aspirin.

19. The compound dosage of claim 17, wherein the protective coating is selected from the group consisting of wax, shellac, hydroxypropyl, methylcellulose phthalate, polyvinyl acetate phthalate and/or cellulose acetate phthalate or a combination thereof.

20. The compound dosage of claim 17, wherein the protective coating is an enteric coating.

21. The compound dosage of claim 17, wherein the aspirin is provided as a single unit in the dosage.

22. The compound dosage of claim 17, wherein the aspirin is provided as multiple units in the dosage.

23. The compound dosage of claim 17, wherein the aspirin is provided in tablet form.

24. The compound dosage of claim 23, wherein the protective coating is an enteric coating substantially surrounding the tablet.

25. The compound dosage of claim 23, wherein the multiple vitamins are provided in loose powder form.

26. The compound dosage of claim 1, wherein the dosage has a shelf life of at least about 365 days.

27. The compound dosage of claim 1, wherein the dosage has a shelf life of at least about 720 days.

28. A compound dosage for the treatment of atherosclerotic cardiovascular disease comprising:
    at least two vitamins selected from the group consisting of ascorbic acid, folic acid, vitamin E, vitamin B6 and vitamin B12;
    zinc;
    an anti-platelet aggregating agent; and
    a protective coating between the anti-platelet aggregating agent and the vitamins and zinc.

29. The compound dosage of claim 28, wherein the anti-platelet aggregating agent comprises aspirin.

30. The compound dosage of claim 29, wherein the protective coating substantially surrounds the aspirin.

31. The compound dosage of claim 29, wherein the protective coating is selected from the group consisting of wax, shellac, hydroxypropyl, methylcellulose phthalate, polyvinyl acetate phthalate and/or cellulose acetate phthalate or a combination thereof.

32. The compound dosage of claim 28, wherein the protective coating is an enteric coating.

33. The compound dosage of claim 29, wherein the aspirin is provided as a single unit in the dosage.

34. The compound dosage of claim 29, wherein the aspirin is provided as multiple units in the dosage.

35. The compound dosage of claim 29, wherein the aspirin is provided in tablet form.

36. The compound dosage of claim 35, wherein the protective coating is an enteric coating substantially surrounding the tablet.

37. The compound dosage of claim 35, wherein the multiple vitamins are provided in loose powder form.

38. The compound dosage of claim 29, wherein the dosage has a shelf life of at least about 365 days.

39. The compound dosage of claim 29, wherein the dosage has a shelf life of at least about 720 days.

40. The compound dosage of claim 28, wherein the dosage comprises from about 90 to about 1,000 milligrams of ascorbic acid, from about 400 to about 1,000 micrograms of folic acid, from about 200 to about 1,200 International Units of vitamin E, from about 3 to about 25 milligrams of vitamin B6, from about 5 to about 500 micrograms of vitamin B12, from about 15 to about 100 milligrams of zinc gluconate, and from about 25 to about 325 milligrams of aspirin.

41. The compound dosage of claim 28, wherein the dosage comprises from about 100 to about 150 milligrams of ascorbic acid, from about 400 to about 800 micrograms of folic acid, from about 300 to about 800 International Units of vitamin E, from about 10 to about 20 milligrams of vitamin B6, from about 8 to about 100 micrograms of vitamin B12, from about 30 to about 50 milligrams of zinc gluconate, and from about 50 to about 300 milligrams of aspirin.

42. A method of making a compound dosage for the treatment of atherosclerotic cardiovascular disease, the method comprising the steps of:
    providing ascorbic acid, folic acid, a minimum of about 200 International Units of vitamin E, vitamin B6 and vitamin B12 in therapeutic amounts effective for the treatment of atherosclerotic cardiovascular disease;
    providing zinc; and
    combining the ascorbic acid, folic acid, vitamin E, vitamin B6, vitamin B12 and zinc with an anti-platelet aggregating agent in dosage form.

43. The method of claim 42, wherein the anti-platelet aggregating agent comprises aspirin.

44. The method of claim 43, wherein the dosage comprises from about 90 to about 1,000 milligrams of ascorbic acid, from about 400 to about 1,000 micrograms of folic acid, from about 200 to about 1,200 International Units of vitamin E, from about 3 to about 25 milligrams of vitamin B6, from about 5 to about 500 micrograms of vitamin B12, from about 15 to about 100 milligrams of zinc gluconate, and from about 25 to about 325 milligrams of aspirin.

45. The method of claim 43, wherein the dosage comprises from about 100 to about 150 milligrams of ascorbic acid, from about 400 to about 800 micrograms of folic acid, from about 300 to about 800 International Units of vitamin E, from about 10 to about 20 milligrams of vitamin B6, from about 8 to about 100 micrograms of vitamin B12, from about 30 to about 50 milligrams of zinc gluconate, and from about 50 to about 300 milligrams of aspirin.

46. The method of claim 43, further comprising providing a protective coating between the aspirin and the multiple vitamins.

47. The method of claim 46, wherein the protective coating comprises an enteric coating.

48. A method of making a compound dosage for the treatment of atherosclerotic cardiovascular disease, the method comprising the steps of:
    providing at least two vitamins selected from the group consisting of ascorbic acid, folic acid, vitamin E, vitamin B6 and vitamin B12;
    providing zinc;
    combining the vitamins and zinc with an anti-platelet aggregating agent in dosage form; and
    providing a protective coating between the anti-platelet aggregating agent and the vitamins and zinc.

49. The method of claim 48, wherein the anti-platelet aggregating agent comprises aspirin.

50. The method of claim 48, wherein the protective coating comprises an enteric coating.

51. The method of claim 48, wherein the dosage comprises from about 90 to about 1,000 milligrams of ascorbic acid, from about 400 to about 1,000 micrograms of folic acid, from about 200 to about 1,200 International Units of vitamin E, from about 3 to about 25 milligrams of vitamin B6, from about 5 to about 500 micrograms of vitamin B12, from about 15 to about 100 milligrams of zinc gluconate, and from about 25 to about 325 milligrams of aspirin.

52. The method of claim 48, wherein the dosage comprises from about 100 to about 150 milligrams of ascorbic acid, from about 400 to about 800 micrograms of folic acid, from about 300 to about 800 International Units of vitamin E, from about 10 to about 20 milligrams of vitamin B6, from about 8 to about 100 micrograms of vitamin B12, from about 30 to about 50 milligrams of zinc gluconate, and from about 50 to about 300 milligrams of aspirin.

53. A method of treating a patient having atherosclerotic cardiovascular disease, the method comprising administering an effective amount of a compound dosage to the patient, the compound dosage comprising:

ascorbic acid, folic acid, a minimum of about 200 International Units of vitamin E, vitamin B6 and vitamin B12 in therapeutic amounts effective for the treatment of atherosclerotic cardiovascular disease;

zinc; and an anti-platelet aggregating agent.

54. The method of claim 53, wherein the anti-platelet aggregating agent comprises aspirin.

55. The method of claim 53, wherein the compound dosage is administered orally to the patient.

56. A method of treating a patient having atherosclerotic cardiovascular disease, the method comprising administering an effective amount of a compound dosage to the patient, the compound dosage comprising:

at least two vitamins selected from the group consisting of ascorbic acid, folic acid, vitamin E, vitamin B6 and vitamin B12;

zinc;

an anti-platelet aggregating agent; and a protective coating between the anti-platelet aggregating agent and the vitamins and zinc.

57. The method of claim 55, wherein the anti-platelet aggregating agent comprises aspirin.

58. The method of claim 56, wherein the compound dosage is administered orally to the patient.

59. A compound dosage for the treatment of atherosclerotic cardiovascular disease comprising:

ascorbic acid, folic acid, vitamin B6, vitamin B12, and a minimum of about 200 International Units of vitamin E;

zinc; and an anti-platelet aggregating agent.

60. A method of making a compound dosage for the treatment of atherosclerotic cardiovascular disease, the method comprising the steps of:

providing ascorbic acid, folic acid, vitamin B6, vitamin B12, and a minimum of about 200 International Units of vitamin E;

providing zinc; and combining the ascorbic acid, folic acid, vitamin B6, vitamin B12, vitamin E and zinc with an anti-platelet aggregating agent in dosage form.

61. A method of treating a patient having atherosclerotic cardiovascular disease, the method comprising administering an effective amount of a compound dosage to the patient, the compound dosage comprising:

ascorbic acid folic acid, vitamin B6, vitamin B12, and a minimum of about 200 International Units of vitamin E;

zinc; and an anti-platelet aggregating agent.

62. A compound dosage for the treatment of atherosclerotic cardiovascular disease comprising:

ascorbic acid, folic acid, vitamin E, vitamin B6 and vitamin B12;

zinc; and an anti-platelet aggregating agent selected from the group consisting of ibuprofen, flubiprofen, ketoprofen, naproxen, tolmetin, fenoprofen, piroxicam, sulindac and mefenamic acid.

63. A method of making a compound dosage for the treatment of atherosclerotic cardiovascular disease, the method comprising the steps of:

providing ascorbic acid, folic acid, vitamin E, vitamin B6 and vitamin B12;

providing zinc; and combining in dosage form the ascorbic acid, folic acid, vitamin E, vitamin B6, vitamin B12 and zinc with an anti-platelet aggregating agent comprising at least one agent selected from the group consisting of ibuprofen, flubiprofen, ketoprofen, naproxen, tolmetin, fenoprofen, piroxicam, sulindac and mefenamic acid.

64. A method of treating a patient having atherosclerotic cardiovascular disease, the method comprising administering an effective amount of a compound dosage to the patient, the compound dosage comprising:

ascorbic acid, folic acid, vitamin E, vitamin B6 and vitamin B12;

zinc; and an anti-platelet aggregating agent comprising at least one agent selected from the group consisting of ibuprofen, flubiprofen, ketoprofen, naproxen, tolmetin, fenoprofen, piroxicam, sulindac and mefenamic acid.

\* \* \* \* \*